US009018580B2

(12) United States Patent
Lemoine et al.

(10) Patent No.: US 9,018,580 B2
(45) Date of Patent: Apr. 28, 2015

(54) METHOD FOR DETECTING MOLECULES THROUGH MASS SPECTROMETRY (75) Inventors: Jérôme Lemoine, Lucenay (FR); Arnaud Salvador, L'Isle D'Abeau (FR); Jean-Philippe Charrier, Tassin-La Demi-Lune (FR); Tanguy Fortin, Bourgoin Jallieu (FR); Philippe Dugourd, Dardilly (FR)

(73) Assignees: bioMerieux, Marcy l'Etoile (FR); Universite Claude Bernard Lyon I, Villeurbanne Cedex (FR); Centre National de la Recherche Scientifique, Paris Cedex (FR)

( * ) Notice: Subject to any disclaimer, the term of this patent is extended or adjusted under 35 U.S.C. 154(b) by 0 days.

(21) Appl. No.: 13/496,949

(22) PCT Filed: Sep. 15, 2010

(86) PCT No.: PCT/FR2010/051919
§ 371 (c)(1),
(2), (4) Date: Apr. 30, 2012

(87) PCT Pub. No.: WO2011/036378
PCT Pub. Date: Mar. 31, 2011

(65) Prior Publication Data
US 2012/0205535 A1    Aug. 16, 2012

(30) Foreign Application Priority Data
Sep. 25, 2009   (FR) ..................................... 09 56662

(51) Int. Cl.
*H01J 49/26*    (2006.01)
*G01N 33/68*    (2006.01)
(Continued)

(52) U.S. Cl.
CPC .......... *G01N 33/6848* (2013.01); *H01J 49/427* (2013.01); *H01J 49/0031* (2013.01); *H01J 49/42* (2013.01)

(58) Field of Classification Search
CPC . G01N 33/6848; H01J 49/0031; H01J 49/427
USPC ......................................................... 250/282
See application file for complete search history.

(56) References Cited

U.S. PATENT DOCUMENTS 5,200,613 A * 4/1993 Kelley ........................... 250/282
5,352,890 A * 10/1994 Johnson et al. ............... 250/282
(Continued)

FOREIGN PATENT DOCUMENTS

DE   10 2007 060 669    7/2008
JP   2005-327579        11/2005
(Continued)

OTHER PUBLICATIONS

Editorial, "Protein Quantitation . . . Biomarker Purgatory?", Clinical Chemistry 54:11, 1749-1752 (2008).
(Continued)

*Primary Examiner* — Nicole Ippolito
*Assistant Examiner* — Wyatt Stoffa
(74) *Attorney, Agent, or Firm* — Clark & Brody (57) ABSTRACT A method for detecting at least one target molecule in a sample by mass spectrometry, comprising ionizing the molecules of the sample and then conducting the following steps (i) and (ii) n times, n being equal to 0, 1, 2, 3 or 4: (i) at least one ion obtained in the preceding step is selected, according to the target molecule, in a mass analyzer, and (ii) the ion thus selected is fragmented in a fragmentation cell; trapping at least two different sampled ions, when n is zero, or when n is other than zero, in a mass analyzer, the at least two ions thus trapped having a mass-to-charge ratio m/z characteristic of the target molecule; ejecting the trapped ions from the mass analyzer; and detecting the ejected ions ejected by means of a detection device. The method is characterized in that the characteristic ions are ejected simultaneously and detected simultaneously.

21 Claims, 5 Drawing Sheets (51) Int. Cl.
*H01J 49/42* (2006.01)
*H01J 49/00* (2006.01)

(56) References Cited

U.S. PATENT DOCUMENTS

| | | | |
|---|---|---|---|
| 7,161,141 B2 | 1/2007 | Mimura et al. | |
| 7,982,182 B2* | 7/2011 | Hashimoto et al. | 250/282 |
| 8,399,827 B1* | 3/2013 | Grothe | 250/282 |
| 8,481,924 B2* | 7/2013 | Savitski et al. | 250/282 |
| 2005/0063864 A1* | 3/2005 | Sano et al. | 422/68.1 |
| 2005/0211891 A1* | 9/2005 | Belov et al. | 250/282 |
| 2005/0253060 A1 | 11/2005 | Mimura et al. | |
| 2007/0069121 A1 | 3/2007 | Mimura et al. | |
| 2009/0114810 A1* | 5/2009 | Green | 250/282 |
| 2009/0127453 A1* | 5/2009 | Ding et al. | 250/282 |
| 2010/0084547 A1* | 4/2010 | Pringle et al. | 250/282 |
| 2011/0057097 A1* | 3/2011 | Bateman et al. | 250/283 |
| 2011/0108725 A1* | 5/2011 | Xu et al. | 250/282 |
| 2013/0112868 A1* | 5/2013 | Schwieters et al. | 250/282 |
| 2013/0292563 A1* | 11/2013 | Green et al. | 250/282 |

FOREIGN PATENT DOCUMENTS

| | | |
|---|---|---|
| JP | 2006-300758 | 11/2006 |
| WO | 99/50669 | 10/1999 |

OTHER PUBLICATIONS

Kulasingam et al., "Product Ion . . . Linear Ion-Trap", Journal of Proteome Research, 2008, 7, 640-647.
Han et al., "Proteomics: from . . . mass spectrometers", Briefings in Functional Genomics and Proteomics, vol. 7, No. 5, 340-354, 2008.
Thevis et al., "Current role . . . doping control", Anal Bioanal Chem. (2007), 388:1351-1358.
Zhang et al., "Mass Spectrometric . . . in Plasma", Molecular & Cellular Proteomics 6.1, 2007 The American Society for Biochem and Molecular Biology, Inc.
Keshishian et al., "Quatitative, Multiplexed . . . Isotope Dilution", Molecular & Cellular Proteomics 6.12, 2007 The American Society for Biochem and Molecular Biology, Inc.
Song et al., "Mass Selection . . . Radiofrequency Quadrupoles", Anal. Chem. 2009, 81, 1833-1840.
Wang et al., "Application of . . . Infant Foods", J. Agric. Food Chem., 2009, 57, 2162-2173.
Duncan et al., "Quatifying proteins . . . the problem", Proteomics 2009, 9, 1124-1127.
Fortin et al., "Clinical Quantitation . . . ELISA Tests", The American Society for Biochemistry and Molecular Biology Inc., Molecular & Cellular Proteomics 8.5, 2009.
Wang et al., "Multiplexed Immunoassay . . . MALDI-TOF MS", Anal. Chem. 2008, 6159-6167.
Pratt et al., "Multiplexed absolute . . . QconCAT genes", Nature Protocols, vol. 1, No. 2, 2006.
Fusaro et al., "Prediction of . . . mass spectrometry", nature biotechnology, vol. 27, No. 2, Feb. 2009.
Mead et al., "MRMaid, the . . . (MRM) Transitions", Molecular & Cellular Proteomics 8.4, 2009, The American Society for Biochem and Molecular Biology, Inc.
Desiere et al., "The PeptideAtlas project", Nucleic Acid Research 2006, vol. 34, Database Issue.
Gerber et al., "Absolute quantification . . . tandem MS", Dept. of Cell biology, Jun. 10, 2003, pp. 6940-6945, vol. 100, No. 12.
Mallick et al., "Computable prediction . . . quantitative proteomics", nature biotechnology, vol. 25, No. 1, Jan. 2007, XP002580668.
March, "An Introduction . . . Mass Spectrometry", Journal of Mass Spectrometry, vol. 32, pp. 351-369 (1997).
Gaskell, "Electrospray: Principles and Practice", Journal of Mass Spectrometry, vol. 32, pp. 677-688 (1997).
Maurer, "Current role . . . forensic toxicology", Anal Bioanal Chem. 388: 1315-1325 (2007).
Schriemer et al., "Detection of . . . Mass Spectrometry", AC Research, Anal. Chem. 1996, 66, 2721-2725.
Kuster et al., "Liquid chromatography . . . and treated waters", journal of Chromatography A, 1216 (2009), 520-529.
Bruns et al., "Isotope-labeled Protein Standards", Molecullar & Cellular Proteomics, The American Society for Biochemistry and Molecular Biology, Inc., 2139-2149, 2007.
Stahl-Zeng et al., "High Sensitivity . . . of N-Glycosites", The American Society for Biochemistry and Molecular Biology, Inc., pp. 1809-1817, 2007.
Anderson et al., "Quatitative Mass . . . Plasma Proteins", The American Society for Biochemistry and Molecular Biology, Inc., pp. 573-588, 2006.
Pico et al., "Control of . . . Food Safety", Mass Spectrometry Reviews, 2006, 25, 917-960.
Anderson et al., "Mass Spectrometric . . . Anti-Peptide Antibodies", Journal of Proteme Research, 2004, 3, 235-244.

* cited by examiner

METHOD FOR DETECTING MOLECULES THROUGH MASS SPECTROMETRY

The present invention relates to the field of techniques for detecting, or even quantifying, chemical and/or biological entities by mass spectrometry.

More particularly, the subject of the present invention is a novel method for detecting at least one target molecule in a sample by mass spectrometry.

Mass spectrometry is a powerful tool for analysing and detecting various types of molecules. Generally, any type of molecule that can be ionized can be detected as a function of its molecular mass using a mass spectrometer. Depending on the nature of the molecule to be detected, some mass spectrometry techniques may be more suitable. By way of non-exclusive example, mention may be made of the use of mass spectrometry of MALDI-TOF type (acronym of Matrix Assisted Laser Desorption Ionization-Time Of Flight) for analysing very large molecules such as polystyrenes (D. Schriemerand L. Li, Analytical Chemistry, 1996, 68; 2721-2725) and the use of tandem mass analysers for quantitatively assaying small molecules in biological fluids (Hans H. Maurer, Analytical and Bioanalytical Chemistry, 2007, 388, 1315-1325).

Documents DE 10 2007 060669 A1, US 2005/063864 A1 and US 2005/211891 A1 illustrate, for example, these techniques and the possible combination thereof.

Regardless of the mass spectrometry method used for the detection, the latter comprises a step of ionization of the target molecule into "molecular" ions, and a step of separation of the molecular ions obtained according to their mass.

All mass spectrometers therefore comprise:
 i) an ionization source intended to ionize the molecules present in the sample to be analysed, i.e. to confer a positive or negative charge on these molecules;
 ii) a mass analyser intended to separate the ionized molecules, or molecular ions, according to their mass-to-charge ratio (m/z);
 iii) a detector intended to measure the signal produced, either directly by the molecular ions, or by ions produced from the molecular ions, as detailed hereinafter.

Separation of the molecular ions according to their m/z ratio can be carried out once (single mass spectrometry or MS), or else several successive MS separations can be performed. When two successive MS separations are carried out, the analysis is called MS/MS or $MS^2$. When three successive MS separations are carried out, the analysis is called MS/MS/MS or $MS^3$ and, more generally, when n successive MS separations are carried out, the analysis is called $MS^n$. Among the techniques implementing several successive separations, the SRM (Selected Reaction Monitoring) mode in the case of assaying a single target molecule, or else the MRM (Multiple Reaction Monitoring) mode in the case of assaying several target molecules, are particular uses of $MS^2$ separation. Similarly, the $MRM^3$ mode is a particular use of separation by MS/MS/MS.

In the case of detection in single MS mode, it is the mass/charge ratio of the molecular ions obtained that is correlated to the target molecule to be detected.

In the case of detection in MS/MS mode, essentially two steps are added compared with an MS assay, namely:
 (i) a fragmentation of the molecular ions, then referred to as precursor ions, so as to give ions termed $1^{st}$-generation fragment ions, and
 (ii) a separation of the ions termed $1^{st}$-generation fragment ions according to their mass.

It is then the mass/charge ratio of the resulting $1^{st}$-generation fragment ions that is correlated to the target molecule to be detected. The term "first-generation fragment ion" is intended to mean an ion resulting from the precursor ion following a fragmentation step, and the mass-to-charge ratio m/z of which is different from the precursor ion.

In any event, the detection of the ions of interest is carried out consecutively at the detector of the analyser, according to the m/z ratios of the ions.

In addition to their detection, mass spectrometry can also make it possible to quantitatively assay one or more target molecules in a sample of interest. Mass spectrometry is a promising technique in the assaying of proteins, which could replace the techniques previously developed, which are in particular ELISAs (Enzyme-linked immunosorbent assays). Among the various known ELISA techniques, the sandwich reaction is the most widely used. It requires two antibodies for the protein of interest, one being linked to the enzyme.

The quantitative assaying of proteins by mass spectrometry techniques, via their proteotypic peptides, which are obtained by digestion of the protein of interest with an enzyme and are specific for the protein of interest, has been validated in complex fluids by the Applicant (T. Fortin et al., MCP, 2008 E-pub) and others (L. Anderson & C. Hunter, MCP, 2006, 573-588; H. Zhang et al., MCP, 2007, 64-71).

Certain modes of use of $MS^2$ separation are particularly suitable for quantitative assaying by mass spectrometry. The SRM and MRM modes thus allow assaying with great sensitivity and great specificity. These $MS^2$ modes can be implemented in a mass spectrometer of triple quadrupole type. The principle of the SRM mode, or else of the MRM mode, is to specifically select a precursor ion, to fragment it, and then to specifically select one of its fragment ions. For such applications, triple quadrupole devices or triple quadrupole ion-trap hybrids are generally used. In the case of a triple quadrupole device (Q1q2Q3) used in $MS^3$ mode, with a view to assaying a target protein, the first quadrupole (Q1) makes it possible to filter the molecular ions, corresponding to the proteotypic peptides characteristic of the protein to be assayed and obtained in a prior digestion step, according to their mass-to-charge ratio (m/z). Only the peptides having the mass/charge ratio of the proteotypic peptide sought, said ratio being referred to as $(m/z)_1$, are transmitted to the second quadrupole (q2) and play the role of precursor ions for the subsequent fragmentation.

The q2 analyser makes it possible to fragment the peptides having a mass/charge ratio $(m/z)_1$ into first-generation fragment ions. The fragmentation is generally obtained by collision of the precursor peptides with an inert gas, such as nitrogen or argon in q2.

The first-generation fragment ions are transmitted to a third quadrupole (Q3) which filters the first-generation fragment ions according to a specific mass-to-charge ratio, said ratio being referred to as $(m/z)_2$. Only the first-generation fragment ions having the mass/charge ratio of a fragment characteristic of the proteotypic peptide sought $(m/z)_2$ are transmitted to the detector in order to be quantified.

This operating mode has a double selectivity, in relation, on the one hand, to the selection of the precursor ion and, on the other hand, to the selection of the first-generation fragment ion. Mass spectrometry in SRM or MRM mode is therefore advantageous for quantification.

The intensity of the current induced by the first-generation fragment ions, measured in the detector, is proportional to the amount of first-generation fragment ions, which is itself proportional to the amount of precursor ions, which is itself proportional to the amount of protein to be assayed. The amount of current measured, induced by the first-generation fragment ions, is therefore directly proportional to the amount of the protein to be assayed. A calibration is nevertheless necessary in order to be able to correlate the amount of current induced by the first-generation fragment ions to the corresponding amount of first-generation fragment ions and, in the end, to the amount of protein to be assayed. The $(m/z)_1$ and $(m/z)_2$ pairs, called transitions, can be assayed in various mass spectrometer models that can operate in the MS/MS mode.

In a device of hybrid triple quadrupole ion-trap type, the operating and analysis mode may be identical to the conventional triple quadrupole mode as presented above. Alternatively, the Q3 quadrupole can then operate in 3D or linear ion-trap mode. Such an ion trap allows selection and gradual, where appropriate continuous, ejection of several $1^{st}$-generation fragment ions $(m/z)_1$ with a view to assaying thereof by variation of the voltage applied to the trap, which causes the radiofrequency voltage in the trap to vary and thus causes resonance of the $1^{st}$-generation fragment ions that it is desired to eject one by one to the detector in order to quantify them.

The advantage of assays by mass spectrometry compared with ELISA assays is a considerable reduction in the cost and time for developing the assay, in particular if antibodies necessary for the ELISA assay must be developed. Such techniques by mass spectrometry therefore appear to be methods of choice for assaying proteins, and make it possible, for example, to more simply and more rapidly validate the clinical interest of assaying the numerous proteins identified as potential markers by research in proteomic analysis (S. Carr & L. Anderson, Clin. Cem. 2008, 1749-1752).

A very large number of non-protein molecules can also be quantitatively assayed by mass spectrometry. Mention may be made of the investigation of doping products (M. Thevis & W. Schanzer, Analytical and Bioanalytical Chemistry, 2007, 388, 1351-1358), contaminants present in the environment (M. Kuster, M. López de Alda, D. Barceló, Journal of chromatography A, 2009, 1216(3), 520-529) or food matrices (Picó Y, Font G, Ruiz M J, Fernández M, Mass spectrometry review, 2006, 25(6), 917-960). By virtue of its sensitivity and its specificity, mass spectrometry makes it possible not only to achieve much lower limits of detection, but also to simplify extraction protocols compared with the former methods of analysis (for example, HPLC-UV). The instrumental progress on ionization sources and interfaces today makes it possible to analyse molecules (for example oestrogens) that were previously analysed by gas chromatography.

In certain cases also, it may be necessary to assay the whole of a family of molecules, or even several families. Several hundred compounds can then be assayed simultaneously (J. Wang J, D. Leung, Journal of Agricultural and Food Chemistry, 2009, 57(6), 2162-73), which is now regularly performed routinely in test laboratories.

Despite the advantages provided by mass spectrometry techniques, the times of the cycles of analysis and detection of the molecules sought generally prove to be relatively long, since the species sought are detected one after the other.

In this context, the objective of the present invention is to propose a method for detecting, or even assaying, molecules by mass spectrometry which allows a significant reduction in the detection cycle times in the analyses by mass spectrometry.

To this end, the invention proposes a novel method for detecting at least one target molecule in a sample by mass spectrometry, in which:

a) the molecules of the sample are ionized, by means of at least one ionization device, so as to obtain molecular ions, b) the following steps (i) and (ii) are carried out n times, n being equal to 0, 1, 2, 3 or 4:
   (i) at least one ion obtained in the preceding step is selected, according to the target molecule, in a mass analyser, and
   (ii) said at least one ion thus selected is fragmented in a fragmentation cell, c) at least two different ions obtained in step a) when n is zero, or in step b) when n is other than zero, are trapped in a mass analyser, said at least two ions thus trapped being characteristic of the target molecule and having a mass-to-charge ratio m/z characteristic of the target molecule, d) said characteristic ions thus trapped are ejected from the mass analyser, and e) said characteristic ions thus ejected are detected by means of a detection device.

Characteristically, in the method according to the invention, the characteristic ions are ejected simultaneously in step d) and detected simultaneously in step e).

The inventors have demonstrated that the ejection and the detection of various ions characteristic of the target molecule, simultaneously, make it possible to considerably reduce the amount of data to be processed and therefore to reduce the cycle and analysis times. By virtue of shorter analysis cycles, it is possible to successively detect a larger number of different molecules. This possibility is particularly advantageous when a multiplexed assay must be carried out.

Furthermore, when a quantitative assay of the target molecule(s) is carried out, surprisingly and particularly advantageously, the inventors have noted that the simultaneous ejection of various ions characteristic of the target molecule, characterized by their m/z ratio, provides a significant improvement in the signal/noise ratio of the detection signal useful for assaying the molecule of interest in the sample tested. This improvement in the signal/noise ratio reduces, moreover, the limit of quantification of the method, in particular in comparison with known MRM methods.

The method according to the invention is suitable for detecting any type of molecule that can be ionized, irrespective of its nature, and in particular for detecting peptides, lipids, glycolipids, glycoproteins, nucleic acids, metabolites, volatile compounds, small molecules of oestrogen type, etc.

The sample on which the method of the invention can be carried out is any sample that may contain a target molecule. The sample may be of biological, either animal, plant or human, origin. It may then correspond to a specimen of biological fluid (whole blood, serum, plasma, urine, cerebrospinal fluid, organic secretion, for example), a tissue specimen or a specimen of isolated cells. This specimen can be used as it is or can undergo, prior to the analysis, a preparation of enrichment, extraction, concentration, purification type, according to methods known to those skilled in the art. The sample may be of industrial origin, i.e., according to a non-exhaustive list, a specimen of air, a specimen of water, a specimen taken from a surface, a component or a manufactured product, or a product of food origin. Among the samples of food origin, mention may be made, in a nonexhaustive manner, of a sample of milk products (yogurts, cheeses), of meat, of fish, of eggs, of fruit, of vegetables, of water or of a drink (milk, fruit juice, soda, etc.). These samples of food origin may also come from prepared dishes or sauces. Finally, a food sample may be derived from an animal feed, such as, in particular, animal meals.

According to one embodiment of the invention, in particular for analysing and detecting proteotypic peptides of proteins, the sample is pretreated for purification purposes.

The pretreatment of samples is widely known to those skilled in the art and may in particular implement electrophoresis or chromatography techniques. These separative techniques can be used alone or combined with one another in order to obtain a multidimensional separation. For example, multidimensional chromatography can be used by combining a separation by ion exchange chromatography with reverse-phase chromatography, as described by T. Fortin et al., above, H. Keshishian et al., above. In these publications, the chromatographic medium may be a column or a cartridge (solid-phase extraction).

The electrophoretic or chromatographic fraction (or the retention time in one-dimensional or multidimensional chromatography) of the proteotypic peptides is characteristic of each peptide and the implementation of these techniques therefore makes it possible to select the proteotypic peptide(s) to be assayed. Such a fractionation of the peptides generated makes it possible to increase the specificity of the subsequent assay by mass spectrometry.

An alternative to the electrophoresis or chromatography techniques, for fractionating the peptides, consists in specifically purifying the N-glycopeptides (J. Stal-Zeng et al., MCP, 2007, 1809-1817 and patent application WO 2008/066629). However, such a purification only allows the quantification of peptides having undergone a post-translational modification of N-glycosylation type. As it happens, not all proteins are glycosylated, which therefore limits its use.

Another alternative for fractionating the peptides consists in immunopurifying the peptide of interest, for example by affinity chromatography. This method makes it possible to drastically reduce the complexity of the sample by obtaining a fraction comprising only the peptide to be assayed (and possibly a few contaminating peptides). Such an approach, called SISCAPA, is described in L. Anderson et al., above, and in patent application US 2004/0072251.

Preferably, the method of the invention, regardless of the variant thereof selected and implemented, proves to be particularly useful and advantageous when the target molecule is a proteotypic peptide of a protein.

In this case, the sample to be analysed has been pretreated to generate peptides from all of the proteins present in an initial sample so as to fragment these proteins into peptides, for example by digestion with a proteolytic enzyme (protease), or through the action of a chemical reagent.

Indeed, protein cleavage can be carried out by means of a physico-chemical treatment, by means of a biological treatment or by means of a combination of the two treatments. Among the treatments that can be used, mention may be made of treatment with hydroxyl radicals, in particular with $H_2O_2$. The treatment with hydroxyl radicals causes a cleavage of the peptide bonds, which takes place randomly on any peptide bond of the protein. The concentration of hydroxyl radicals conditions the number of cleavages carried out and therefore the length of the peptide fragments obtained.

Other chemical treatments can also be used, such as, for example, treatment with cyanogen bromide (CNBr) which specifically splits the peptide bonds at the level of the carboxylic group of methionyl residues. It is also possible to carry out a partial acidic cleavage at the level of the aspartyl residues by heating at 1000° C a solution of proteins in trifluoroacetic acid.

Treatment of the proteins by enzymatic digestion is nevertheless preferred. Compared with physicochemical treatment, it provides greater preservation of the structure of the proteins, and is easier to control. The term "enzymatic digestion" is intended to mean the simple or combined action of one or more enzymes under suitable reaction conditions. The enzymes performing the proteolysis, called proteases, cleave the proteins at specific sites. Each protease generally recognizes a sequence of amino acids within which it always performs the same cleavage. Certain proteases recognize a single amino acid or a sequence of two amino acids between which they perform a cleavage; other proteases recognize only longer sequences. These proteases may be endoproteases or exoproteases. Among the known proteases, mention may be made, as described in WO 2005/098071, of:

specific enzymes, such as trypsin which splits the peptide bond at the carboxylic group of Arg and Lys residues, endolysin which cleaves the peptide bond of the —CO group of lysines, chymotrypsin which hydrolyses the peptide bond at the carboxylic group of aromatic residues (Phe, Tyr and Trp), pepsin which cleaves at the $NH_2$ group of aromatic residues (Phe, Tyr and Trp), and the V8 protease of the V8 strain of *Staphylococcus aureus*, which cleaves the peptide bond at the carboxylic group of the Glu residue;

nonspecific enzymes, such as thermolysin originating from the bacterium *Bacillus thermoproteolyticus*, which hydrolyses the peptide bond of the $NH_2$ group of hydrophobic amino acids (Xaa-Leu, Xaa-Ile, Xaa-Phe), subtilisin and pronase which are bacterial proteases that hydrolyse practically all the bonds and can convert proteins into oligopeptides under controlled reaction conditions (enzyme concentration and reaction time).

Several proteases can be used simultaneously, if their modes of action are compatible, or they can be used successively. In the context of the invention, the digestion of the sample is preferably carried out by the action of a protease enzyme, for example trypsin.

Such a treatment step makes it possible to convert the large molecules represented by the proteins present in the initial sample, into peptides, which are smaller molecules and which will be present in the sample of interest. The sensitivity of the detection subsequently obtained by mass spectrometry is thus increased. In addition, the treatment step makes it possible to generate several proteotypic peptides, also called reporter peptides, for a given target protein.

The specificity of each proteotypic peptide must, moreover, be verified by making sure, for example, that no other protein comprises an identical peptide sequence, or that no other transition interferes. The treatment thus makes it possible to increase the possibility of obtaining one or more proteotypic peptides specific for the protein to be assayed. Each proteotypic peptide makes it possible to quantify the protein by means of an independent assay.

Moreover, most commonly, in order to ensure sensitivity and specificity compatible with the assaying of a protein at a concentration of a few ng/ml in a complex fluid (blood, serum, plasma, urine, stool, sputum, etc.), the quantitative assaying by mass spectrometry should be preceded, in addition to the digestion step, with other steps interspersed around the digestion step, for instance:

Phase 1: protein fractionation in order to eliminate the predominant proteins, not corresponding to the target protein, or else a purification of the sample by any suitable technique: electrophoresis, chromatography, immunocapture (Kulasingam et al., J. Proteome Res., 2008, 640-647). However, the latter technique requires the existence or the preparation of a specific antibody directed against the target protein, which can be lengthy and expensive to obtain. Furthermore, the subsequent performance levels of the assay by mass spectrometry will be in part linked to the quality and to the specificity of the antibody.

Phase 2: denaturation, reduction and blocking of thiol functions.

Phase 3: digestion.

Phase 4: peptide fractionation.

Phase 2 makes it possible to increase the digestion yield and ensures better robustness of the assay, in terms of reproducibility and reliability. Phases 1 and 4 are optional when a great sensitivity is not required (L. Anderson & C. Hunter, MCP, above). On the other hand, they are essential when great sensitivity is necessary (a few ng/ml). This is what was demonstrated by T. Fortin et al., above, H. Keshishian et al., MCP, 2007, 2212-2229 and V. Kulasingam et al., J. Proteome Res., 2008, 640-647, L. Anderson et al., J. Proteome Res., 2004, 235-2344 and US 2004/0072251. Moreover, separation of the peptides by chromatography upstream of the mass spectrometry provides an additional level of specificity by reducing the number of contaminated peptides (M. Duncan et al., Proteomics, 2009, 9:1124-1127).

In the method of the invention, the ionization step a) carried out may be implemented by any method known to those skilled in the art. The ionization source makes it possible to vaporize the molecules and to ionize them. An ionization source can be used either in positive mode for studying positive ions, or in negative mode for studying negative ions. Several types of sources exist and will be used depending on the desired result and on the molecules analysed. Mention may in particular be made of:

- electron ionization (EI), chemical ionization (CI) and desorption-chemical ionization (DCI),
- fast atom bombardment (FAB), metastable atom bombardment (MAB) or ion bombardment (SIMS, LSIMS),
- inductively coupled plasma (ICP),
- atmospheric pressure chemical ionization (APCI) and atmospheric pressure photoionization (APPI),
- electrospray ionization (ESI),
- matrix-assisted laser desorption ionization (MALDI), surface enhanced laser desorption ionization (SELDI) or desorption/ionization on silicon (DIOS),
- ionization-desorption by interaction with metastable species (DART).

In particular, the ionization can be carried out as follows: the sample containing the target molecules is introduced into an ionization source, where the molecules are ionized in the gas state and thus converted into molecular ions which correspond to the initial molecules. An ionization source makes it possible to ionize a molecule and to obtain molecular ions which then correspond to the molecules present in the liquid state, with, in the positive mode, one, two, or even three additional protons or more, and therefore carry one, two or even three charges or more.

For example, when the target molecule is a protein, ionization of the proteotypic peptides obtained after fractionation of the target protein, by virtue of a source of electrospray type operating in the positive mode, results in polypeptide ions in the gas state, with one, two, or even three additional protons or more, and which therefore carry one, two, or even three charges or more, and allows a change from a liquid state to a gas state (Gaskell, Electrospray: principles and practise, J. Mass Spectrom. (1997), 32, 677-688). This type of source is particularly suitable when the target molecules or proteotypic peptides obtained are separated beforehand by reverse-phase liquid chromatography. Nevertheless, the yield from ionization of the molecules present in the sample can vary according to the concentration and the nature of the various species present. This phenomenon results in a matrix effect well known to those skilled in the art.

A MALDI ionization source will make it possible to ionize molecules from a sample in the solid state.

The mass analyser in which the trapping step b) of the method according to the invention is carried out makes it possible to separate the ions according to their mass/charge ratio (m/z).

Any mass analyser known to those skilled in the art may be used. Mention may be made of low-resolution analysers, of the quadrupole (Q), 3D ion trap (IT) or linear ion trap (LIT) type, and high-resolution analysers, for measuring the exact mass of the analytes and which use in particular the magnetic sector coupled to an electrical sector, the time of flight (TOF).

In accordance with a preferred feature of the method of the invention, the mass analyser used in step c) is an ion trap. Such an ion trap has the advantage of allowing both selection of the ions according to their m/z ratio, but also simultaneous ejection of the ions of which the m/z ratio is characteristic of the target molecule of interest. Advantageously, this ion trap may be of 3D or linear type.

Through the use of such an ion trap, the ejection of the ions of which the mass-to-charge ratio m/z is characteristic of the target molecule is then carried out by making said ions simultaneously resonate in the ion trap by means of radiofrequencies. These radiofrequencies are emitted by variations in the supply voltages of constituent electrodes of the ion trap. A broadband of radiofrequencies comprising all the radiofrequencies of the ions to be expelled can, for example, be applied. It is possible for the radiofrequency range used to correspond to the superposition of a set of radiofrequency bands, each being centred on the characteristic oscillation frequency in the trap of the ion to be expelled, or frequency of its secular motion (R. E. March, Int. J. Mass Spectrom., 1997, 32: 351.).

Preferably, each band will correspond to a radiofrequency band centred on the characteristic frequency of the secular motion of an ion to be expelled. Simultaneous ejection of various ions, having different mass-to-charge ratio m/z values, is thus obtained.

In accordance with another preferred feature of the method of the invention, the mass analyser is emptied before ejection and detection of the ions having the mass-to-charge ratio m/z characteristic of the target molecule. A broadband of radiofrequencies that does not comprise the radiofrequencies of the characteristic ions that will subsequently be expelled may, for example, be applied. The radiofrequency range used will not comprise a set of radiofrequency bands, each centred on the characteristic frequency of the secular motion of a characteristic ion.

Preferably, each absent band will correspond to a radiofrequency band centred on the characteristic frequency of the secular motion of a characteristic ion. Simultaneous ejection of all the ions present in the mass analyser is thus obtained, with the exception of the various characteristic ions selected, which will be subsequently ejected.

The method of the invention may be an $MS^{n+1}$ according to the value of n, n being an integer corresponding to the number of times the fragmentation steps are carried out.

Thus, when the method of the invention is a single MS, n is equal to zero, there is no step b) and the method comprises the following steps:

a) the molecules of the sample are ionized, by means of at least one ionization device, so as to obtain molecular ions, and c) at least two different ions obtained in step a) are trapped in a mass analyser, said at least two ions thus trapped being characteristic of the target molecule and having a mass-to-charge ratio m/z characteristic of the target molecule, d) said characteristic ions thus trapped are ejected from the mass analyser, and e) said characteristic ions thus ejected are detected by means of a detection device, it being understood that the characteristic ions are ejected simultaneously in step d) and detected simultaneously in step e).

When the method of the invention is not a single MS, then n is equal to 1, 2, 3 or 4.

According to one implementation variant, the method of the invention is an MS/MS, such that n is 1 and the at least two different ions trapped in step c) are first-generation fragment ions.

In this case, the method of the invention comprises the following steps:
a) the molecules of the sample are ionized, by means of at least one ionization device, so as to obtain molecular ions,
b) the following steps (i) and (ii) are carried out once:
  (i) at least one ion obtained in the preceding step, called precursor ion, is selected, according to the target molecule, in a mass analyser, and
  (ii) said at least one ion thus selected is fragmented in a fragmentation cell, so as to give at least two $1^{st}$-generation fragment ions,
c) at least two different ions obtained in step b) are trapped in a mass analyser, said at least two ions thus trapped being characteristic of the target molecule and having a mass-to-charge ratio m/z characteristic of the target molecule,
d) said characteristic ions thus trapped are ejected from the mass analyser, and
e) said characteristic ions thus ejected are detected by means of a detection device,
it being understood that the characteristic ions are ejected simultaneously in step d) and detected simultaneously in step e).

In this case, the mass analyser used for selecting ions according to their mass in step b) is any mass analyser known to those skilled in the art, such as an ion trap or a quadrupole analyser.

The fragmentation of the ions selected is carried out by collision with a neutral gas, such as argon or nitrogen, photoexcitation or photodissociation by means of an intense light source, collision with electrons or free-radical species, application of a potential difference, or any other activation mode. The fragmentation of the ions is carried out in a fragmentation cell such as the models of triple quadrupole type (L. Anderson & C. Hunter, MCP, 2006, 573-588), or of ion trap type (B. Han & R. Higgs, Brief Funct Genomic Proteomic. 2008 September; 7(5):340-54), or else of time-of-flight (TOF) type (K.-Y. Wang et al., Anal Chem, 2008, 80(16) 6159-6167), which also enable ion separation.

When the fragmentation(s) is (are) carried out by collision with an inert gas, such as nitrogen or argon, this is done within an electric field, or else solely by the application of a difference in potential, for example in a time-of-flight tube. The characteristics of the electric field condition the intensity and the nature of the fragmentation. Thus, the electric field applied in the presence of an inert gas, for example in a quadrupole, conditions the collision energy supplied to the ions. This collision energy will be optimized, by those skilled in the art, so as to increase the sensitivity of the transition to be assayed according to the spectrometric device used. By way of example, it is possible to vary the collision energy between 5 and 180 e$^-$V in q2 in an AB SCIEX QTRAP® 5500 mass spectrometer from the company Applied Biosystems (Foster City, United States of America). Similarly, the duration of the collision step and the excitation energy within, for example, an ion trap will be optimized by those skilled in the art, so as to result in the most sensitive assay possible. By way of example, it is possible to vary this duration, called excitation time, between 0.010 and 50 ms and the excitation energy between 0 and 1 (arbitrary unit) in Q3 in an AB SCIEX QTRAP® 5500 mass spectrometer from the company Applied Biosystems.

According to another variant, the method of the invention is an MS/MS/MS such that n is 2 and the at least two different ions trapped in step c) are second-generation fragment ions.

In this case, the method of the invention comprises the following steps:
a) the molecules of the sample are ionized, by means of at least one ionization device, so as to obtain molecular ions,
b) the following steps are carried out:
  (i) at least one ion obtained in the preceding step, called precursor ion, is selected, according to the target molecule, in a mass analyser, and
  (ii) said at least one ion thus selected is fragmented in a fragmentation cell, so as to give a $1^{st}$-generation fragment ion, then
  (iii) at least one $1^{st}$-generation fragment ion is selected, according to the target molecule, in a mass analyser, and
  (iv) said at least one ion thus selected is fragmented in a fragmentation cell, so as to give at least two second-generation fragment ions,
c) at least two different second-generation fragment ions obtained in step b) are trapped in a mass analyser, said at least two ions thus trapped being characteristic of the target molecule and having a mass-to-charge ratio m/z characteristic of the target molecule,
d) said characteristic ions thus trapped are ejected from the mass analyser, and
e) said characteristic ions thus ejected are detected by means of a detection device,
it being understood that the characteristic ions are ejected simultaneously in step d) and detected simultaneously in step e).

In this case, the mass analysers used for selecting ions according to their mass in step b) are any mass analyser known to those skilled in the art, such as an ion trap or a hybrid triple quadrupole (Q1q2Q3) ion-trap analyser, which differs from the quadrupole analyser in that the quadrupole Q3 then operates in 3D or linear ion-trap mode.

When the method according to the invention implements tandem mass spectrometry ($MS^2$, $MS^3$, $MS^4$ or $MS^5$), several mass analysers can thus be coupled together. For example, a first analyser separates the ions, a collision cell makes it possible to fragment the ions, and a second analyser separates the fragment ions. Some analysers, such as ion traps or FT-ICR, constitute several analysers in one and make it possible to fragment the ions and to analyse the fragments directly.

The method of the invention can in particular, but not exclusively, be applied to spectrometric techniques termed $MRM^3$. With such techniques, an experimental analyser configuration of hybrid triple quadrupole ion-trap type is the most commonly used. This mass spectrometry configuration exhibits very good selectivity and good sensitivity of detection, which are very important in particular for carrying out a good quantification of proteins in complex samples such as samples of biological fluids.

According to the preferred embodiments of the invention, in which the analysis carried out is of $MS^{n+1}$ type and where n is equal to 1, 2, 3 or 4:
the mass analyser used in step b) is an ion trap or a quadrupole,
the fragmentation cell is an ion trap or a quadrupole.

According to another preferred embodiment of the invention, in a mode other than single MS, steps b) and c) are carried out in a single device, namely in an ion trap, which simplifies the material used.

Generally, it is also possible to envision and to carry out, in the method of the invention, the simultaneous ejection of the specific fragment ions and their simultaneous detection prior to the ejection of the contaminating ions present in the ion trap. In this case, a broad-band radiofrequency wave, not comprising the radiofrequencies of the characteristic ions that will subsequently be expelled, is applied.

The method is also of interest in a device in accordance with that published recently by the group of G. Cooks [Q. Song et al. *Anal. Chem*, 2009, 81, 1833-1840] for the simultaneous transmission, in a quadrupole, of molecular ions having different m/z values resulting from the ionization of the same molecule. In this case, it is possible to simultaneously trap and to fragment two molecular ions from the same molecule in order to simultaneously eject the fragment ions resulting from the fragmentation of the two molecular ions.

The choice of the characteristic ions which are detected so as to be correlated to the target molecule is made by those skilled in the art according to standard methods. Their selection will advantageously result in assays that are as sensitive as possible, as specific as possible and as robust as possible in terms of reproducibility and reliability. In the methods developed for selecting proteotypic peptides $(m/z)_1$, and first-generation fragments $(m/z)_2$, the choice is essentially based on the intensity of the response. For further details, reference may be made to V. Fusaro et al., Nature Biotech. 27; 2009; 190-198. Commercial software, such as the MIDAS and MRM Pilot software from Applied Biosystemsor elseMR-Maid (J. Mead et al., MCP, 15 Nov. 2008, E-pub) may be used by those skilled in the art, in order to enable them to predict all the possible transition pairs. They may also make use of a database called PeptideAtlas constructed by F. Desiere et al., (Nucleic Acids Res. 2006, January 1; 34(database issue): D655-8) in order to compile all the peptide MRM transitions described by the scientific community. This PeptideAtlasbase is available with free access on the internet. For non-protein molecules, it is also possible to use databases, such as, for example, the base of 400 pesticides accessible through the Cliquidsoftware from the company Applied Biosystems (United States of America).

The detection of the characteristic ions selected in step e) is carried out conventionally, in particular by means of a detector and a processing system. The detector collects the ions ejected and produces an electrical signal, the strength of which depends on the amount of ions collected, this signal then being amplified so that it can be computer-processed. The greater the number of ions, the higher the current. The electrical signal obtained therefore corresponds to all the collected ions which are simultaneously ejected into the detector.

The processing system that is combined with the detector is conventionally a data-processing computer system which makes it possible to analyse and quantify the information received by the detector, in this case the intensity of the current induced by the ions selected, this intensity of induced current being proportional to the amount of target molecule.

It is thus possible to quantify, after simultaneous ejection and simultaneous detection, the characteristic ions detected, in order to quantify the target molecule.

A calibration is nevertheless necessary in order to be able to correlate the amount of current induced by the detected ions to the amount of target molecule to be assayed. The intensity of current thus measured may serve as a quantitative measurement for determining the amount of target molecule present, which is characterized by its expression in the International System of units (SI units) of mol/m$^3$ or kg/m$^3$ type, or by multiples or submultiples of these units, or by the usual derivatives of SI units, including multiples and submultiples thereof. By way of nonlimiting example, units such as ng/ml or fmol/l are units characterizing a quantitative measurement.

For this, the calibrations conventionally used in mass spectrometry may be implemented in the context of the invention. MRM assays are conventionally calibrated using external standards or, preferably, using internal standards as described by T. Fortin et al., above. When the target molecule is a proteotypic peptide, making it possible to assay a protein of interest, the correlation between the quantitative measurement and the amount of target proteotypic protein, and subsequently of protein of interest, is obtained by calibrating the signal measured relative to a standard signal for which the amount to be assayed is known. The calibration can be carried out by means of a calibration curve, for example obtained by means of successive injections of standard proteotypic peptide at various concentrations (external calibration) or, preferentially, by internal calibration using a heavy peptide, as an internal standard, for example in accordance with the AQUA, QconCAT or PSAQ methods detailed hereinafter. The term "heavy peptide" is intended to mean a peptide corresponding to the proteotypic peptide, but in which one or more carbon 12 ($^{12}$C) atoms is (are) replaced with carbon 13 ($^{13}$C), and/or one or more nitrogen 14 ($^{14}$N) atoms is (are) replaced with nitrogen 15 ($^{15}$N).

The use of heavy peptides, as internal standards (AQUA), has also been proposed by S. A. Gerber et al., above and in patent application US 2004/0229283. The principle is to artificially synthesize proteotypic peptides with amino acids comprising isotopes that are heavier than the usual natural isotopes. Such amino acids are obtained, for example, by replacing some of the carbon 12 ($^{12}$C) atoms with carbon 13 ($^{13}$C), or by replacing some of the nitrogen 14 ($^{14}$N) atoms with nitrogen 15 ($^{15}$N). The artificial peptide (AQUA) thus synthesized has rigorously the same physicochemical properties as the natural peptide (with the exception of a higher mass). It is generally added to the sample, at a given concentration, upstream of the assaying by mass spectroscopy, for example between the treatment leading to the cleavage of the proteins of the sample of interest and the fractionation of the peptides obtained after the treatment step. As a result, the AQUA peptide is copurified with the natural peptide to be assayed, during the fractionation of the peptides. The two peptides are therefore injected simultaneously into the mass spectrometer, for the assay. They then undergo the same ionization yields in the source. The comparison of the areas of the peak of the natural peptide and the AQUA peptide, the concentration of which is known, makes it possible to calculate the concentration of the natural peptide and thus to work back to the concentration of the protein to be assayed. A variant of the AQUA technique has been proposed by J.-M. Pratt et al. (Nat. Protoc. 2006, 1:1029-1043) under the nameQconCat. This variant is also described in patent application WO 2006/128492. It consists in concatenating various AQUA peptides and in producing the artificial polypeptide in the form of a heavy recombinant protein. The recombinant protein is synthesized with amino acids comprising heavy isotopes. In this way, it is possible to obtain a standard for calibrating the simultaneous assaying of several proteins at a lower cost. The QconCAT standard is added from the beginning, upstream of the treatment leading to the cleavage of the proteins and before the steps of protein fractionation, denaturation, reduction and then blocking of the thiol functions of the proteins, if said steps are present. The QconCAT standard therefore undergoes the same treatment cycle, leading to the same cleavage of the proteins as the natural protein, which makes it possible to take into account the yield of the treatment step leading to the cleavage of the proteins. Indeed, the treatment, in particular by digestion, of the natural protein may not be complete. In this case, the use of an AQUA standard would result in the amount of natural protein being underestimated. For absolute assaying, it may therefore be important to take into account the yields from treatment leading to the cleavage of the proteins. However, V. Bruni et al. (MCP, 2007, 2139-2149) have shown that, sometimes, the QconCAT standards do not exactly reproduce the yield from treatment, in particular by digestion, of the natural protein, doubtless because of a different three-dimensional conformation of the QconCAT protein.

V. Brun et al., above, have therefore proposed using a method called PSAQ and described in patent application WO 2008/145763. In this case, the internal standard is a recombinant protein, having the same sequence as the natural protein but synthesized with heavy amino acids. The synthesis is carried out ex vivo with heavy amino acids. This standard has rigorously the same physicochemical properties as the natural protein (with the exception of a higher mass). It is added from the beginning, before the protein fractionation step, when the latter is present. It is therefore copurified with the native protein, during the protein fractionation step. It exhibits the same yield from treatment, in particular by digestion, as the native protein. The heavy peptide obtained after cleavage is also copurified with the natural peptide, if a peptide fractionation step is carried out. The two peptides are therefore injected simultaneously into the mass spectrometer, so as to be assayed quantitatively. They then undergo the same ionization yields in the source. Comparison of the peak areas of the natural peptides and of the reference peptides in the PSAQ method makes it possible to calculate the concentration of the protein to be assayed while taking into account all of the steps of the assaying method.

All of these techniques, namely AQUA, QconCAT or PSAQ or any other calibration technique, used in assays by mass spectrometry and in particular in MRM or MS assays, may be implemented in order to perform the calibration, in the context of the invention.

The method of the invention and advantages thereof will emerge from the rest of the present description relating three exemplary embodiments of the method of the invention in the context of analyses by mass spectrometry of various biological solutions. These examples make reference to the appended figures among which.

In the examples described hereinafter, the method of the invention was carried out using an AB Sciex QTRAP® 5500 LC/MS/MS triple quadrupole ion-trap analytical device from the company Applied Biosystems (Foster City, United States of America).

EXAMPLE 1

Verification of the Purity of a Recombinant Protein by Simultaneous Expulsion of Reporter Proteotypic Peptides in an Ion Trap. MS Analysis The TP171 recombinant protein is a recombinant protein of *Treponema pallidum*, the agent responsible for syphilis, having the sequence SEQ ID No. 1.

```
SEQ ID No. 1:
MRGSASFSSIPNGTYRATYQDFDENGWKDFLEVTFDGGKMVQVVYDYQH

KEGRFKSQDADYHRVMYASSGIGPEKAFRELADALLEKGNPEMVDVVTG

ATVSSQSFRRLGAALLQSARRGEKEAIISRGSSKYKYHHHHHH.
```

3 batches of the TP171 recombinant protein are digested according to the following protocol:
Dilution of the TP171 solutions so as to obtain a final concentration of 10 μg/ml in 3 ml of 50 mM bicarbonate, pH=8.0.
Addition of dithiothreitol (DTT) so as to obtain a final concentration of 15 mM.
Reduction to 60° C. for 40 minutes.
Cooling of the tubes to ambient temperature.
Addition of iodoacetamide so as to obtain a final concentration of 25 mM.
Alkylation for 40 minutes at ambient temperature and in the dark.
Addition of trypsin with a ratio of 1/30.
Digestion at 37° C. for 4 hours.
Addition of DTT so as to obtain a final concentration of 10 mM.
Reduction at 60° C. for 40 minutes.
Cooling of the tubes to ambient temperature.
Addition of acetonitrile (ACN) and of formic acid so as to obtain a final concentration of 10% of ACN and 0.5% of formic acid.

The resulting sample is directly injected continuously into the ionization source of an AB Sciex QTRAP® 5500 mass spectrometer at a flow rate of 10 μl/min. The triple quadrupole of the mass spectrometer is used in the ion trap mode only, such that the quadrupoles merely serve to guide the ions in the trap of the quadrupole Q3.

The simultaneous expulsion mode used in the method of the present invention is compared with the EMS (Enhanced Mass Spectrometry) mode consisting in performing a scan in the trap in order to successively expel all the ions.

The other machine parameters used are reproduced in TABLE 1 below:

TABLE 1

| Polarity | Positive |
|---|---|
| Ionization source | Turbo V ™ (Applied BioSystems) |
| Linear ion trap fill time in Q3 | Between 0.05 and 250.00 ms |
| Curtain gas pressure | 30.00 psi |
| Cone voltage | 5500.00 V |
| Nebulising gas pressure | 25.00 psi |

The total signal observed is measured (Total Ion Count, TIC). All of the ions present in the sample contribute to this signal observed.

Figure 1:
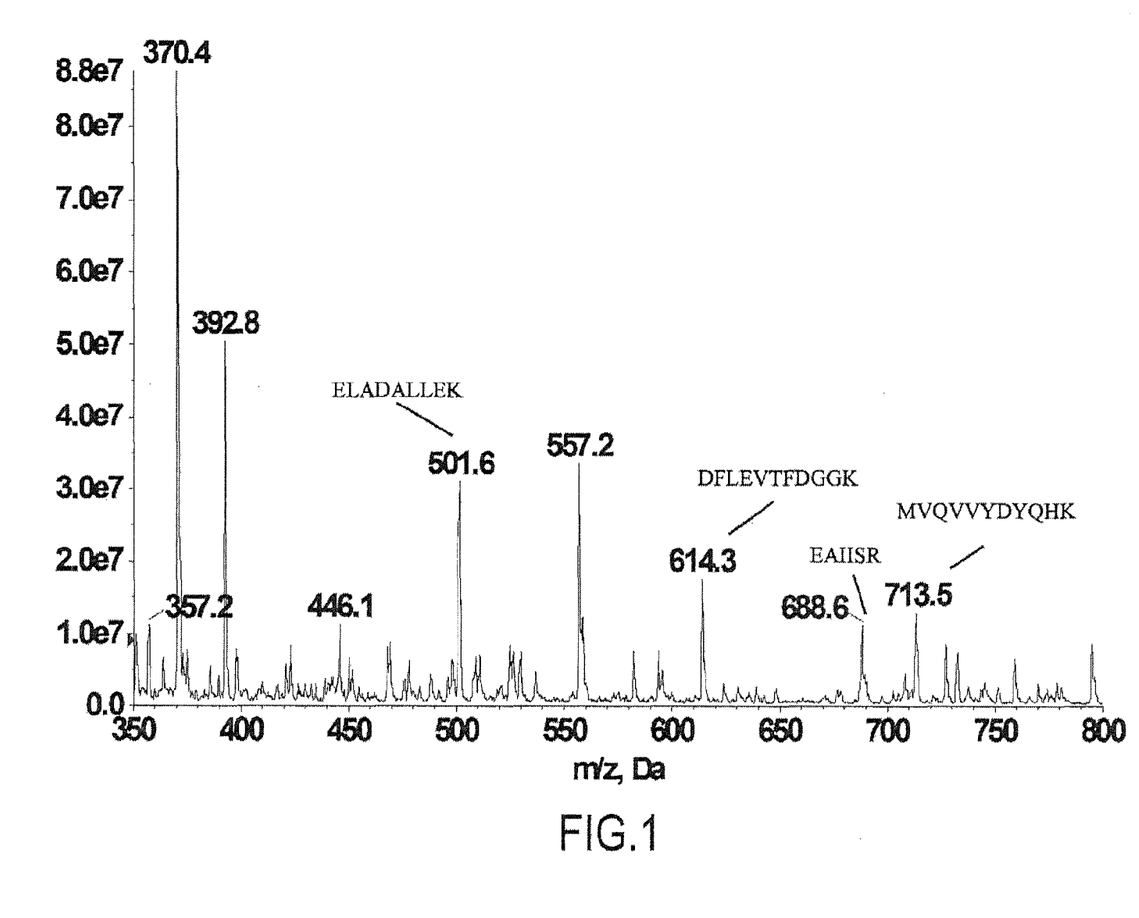
FIG. 1 represents an MS mass spectrum of batch No. 1 of TP171 proteins, used in example 1.

In EMS mode, the total signal can be broken down so as to obtain the mass spectrum, represented in FIG. 1 for batch No. 1, by means of a scan of all the masses. Between 350 and 800 Th, the scan time is 450.1 ms at a speed of 1000 Da/s.

The mixture analysed contains contaminating ions and proteotypic ions, the latter being characteristic of the TP171 protein. These proteotypic ions and the characteristic mass-to-charge ratio m/z thereof are reported in TABLE 2 thereinafter.

TABLE 2

| Proteotypicion | Sequence | m/z |
|---|---|---|
| ELADALLEK | SEQ ID No. 2 | 501.6 (doubly charged ion) |
| DFLEVTFDGGK | SEQ ID No. 3 | 614.3 (doubly charged ion) |
| EAIISR | SEQ ID No. 4 | 688.6 (singly charged ion) |
| MVQVVYDYQHK | SEQ ID No. 5 | 713.4 (doubly charged ion with an oxidized methionine) |

A ratio, reported in TABLE 3, is produced by dividing the signal obtained with all the proteotypic ions by the signal obtained with the total ions (contaminating ions+proteotypic ions).

TABLE 3

| TP171 batch | Proteotypic ions/total ions ratio |
|---|---|
| 1 | 0.068 |
| 2 | 0.069 |
| 3 | 0.047 |

The resulting ratios are values representative of the purity of the sample with respect to TP171. They therefore make it possible to easily and rapidly estimate the purity of a batch of TP171 in comparison with a reference batch. Thus, batch No. 2 has a purity similar to batch No. 1 (reference batch), whereas batch No. 3 is less pure.

Alternatively and by comparison, the same experiment is carried out according to the method of the present invention. The proteotypicions are simultaneously ejected, more simply and more rapidly (1.6 ms), by applying to one or more electrodes a superposition of radiofrequency voltages. For each proteotypic ion, a frequency notch centred on the characteristic frequency of the secular motion of this ion is applied. The frequency width of the notch corresponds to a window of 0.7 mass unit around the theoretical mass of each ion. The voltage applied is therefore the sum of these various notches.

The masses of the proteotypic ions expelled and detected simultaneously are given in TABLE 2.

The broadband wave thus applied leads to the ejection of all the proteotypic ions in 0.8 ms. The signal S1 obtained is measured. Simultaneous expulsion of all the remaining ions trapped in the trap is then carried out in order to empty it, also in 0.8 ms. The signal S2 obtained is measured.

The calculation S1 divided by (S1+S2) is then performed.

It is noted, when establishing this signal ratio, that exactly the same values as those obtained in TABLE 3 using the EMS method are obtained.

The assay method of the present invention therefore allows an assay of TP171 via these proteotypic ions that is as precise as the EMS method, but in a much shorter period of time.

EXAMPLE 2

Measurement of the Concentration of a Protein at High Concentration in a Complex Mixture with an AB Sciex QTRAP® 5500 LC/MS/MS Mass Spectrometer Having a Triple Quadrupole Q1q2Q3 Configuration with One Fragmentation Cycle, and the Quadrupole Q3 of which Operates in Ion-Trap Mode. MS/MS Analysis Five milligrams of PSA (Prostate Specific Antigen, supplied by the English company Scipac), reference P117-8, are digested according to the protocol of example 1.

One milliliter of female serum not containing PSA is also digested according to the protocol of example 1. The female serum was obtained from the Etablissement Franøais du Sang [French Blood Bank]. Except for particular pathological cases, women do not synthesize PSA. Female sera do not therefore generally contain PSA. The absence of PSA in the female serum used here was verified beforehand by means of the Vidas TPSA assay from the company bio Mérieux S. A. (Marcy l'Etoile, France).

After digestion, the female serum solution digested is divided up into various aliquots which are supplemented with the solution of digested PSA so as to obtain solutions with a concentration of 500, 200, 100, 50 and 0 µg/ml of PSA.

A volume of 100 µl of the resulting aliquots is injected and analysed according to the following conditions:

Ultimate 3000 chromatographic system from the company Dionex (Sunnyvale, Calif., United States of America)

C18 symmetry column, 2.1 mm internal diameter, 100 mm long, 3.5 µm particle size, from the company Waters (Milford, Mass., United States of America)

Solvent A: $H_2O$+0.1% formic acid

Solvent B: ACN+0.1% formic acid.

An HPLC gradient defined in TABLE 4 hereinafter is applied for the chromatographic analysis:

TABLE 4

| Time | Flow rate (µl) | Solvent A (%) | Solvent B (%) |
|---|---|---|---|
| 0 | 300 | 95 | 5 |
| 3 | 300 | 95 | 5 |
| 15 | 300 | 78 | 22 |
| 16 | 300 | 0 | 100 |
| 24 | 300 | 0 | 100 |
| 24.1 | 300 | 95 | 5 |
| 32 | 300 | 95 | 5 |

The chromatographic column output eluate is directly injected into the ionization source of the mass spectrometer.

The quadrupole Q1 of the mass spectrometer is used to specifically select the ions of 636.8 Th, with a resolution of 0.7 mass unit. These ions are molecular ions of at least one peptide having the sequence LSEPAELTDAVK (SEQ ID No 6), resulting from a proteolytic hydrolysis with trypsin, according to the method of example 1, of the PSA protein introduced into a female serum at final concentrations of between 100, 50, 10, 5 and 0 µg/ml of PSA.

This peptide sequence, called reporter sequence, serves as a support for the PSA protein assay.

The quadrupole q2 is used to fragment the ions of 636.8 Th into first-generation fragments. The ions selected in Q1 are subjected in q2 to a collisional activation process, in order to cause fragmentation thereof into neutral fragments and into first-generation fragment ions, the most intense of which have m/z values of 943.5, 846.5, 775.4 and 312.2 Th.

All of the fragment ions leaving the quadrupole q2 are transferred into the quadrupole Q3, which is an ion trap operating in ion-trap mode, where they will be trapped.

The other machine parameters used are the same as those of example 1.

The simultaneous expulsion mode of the present invention is then compared with the EPI (Enhanced Product Ion) analysis mode.

This EPI analysis mode comprises in Q3 a scan of between 300 and 1000 Th, carried out in the ion trap in order to successively expel all the ions.

Figure 2A:
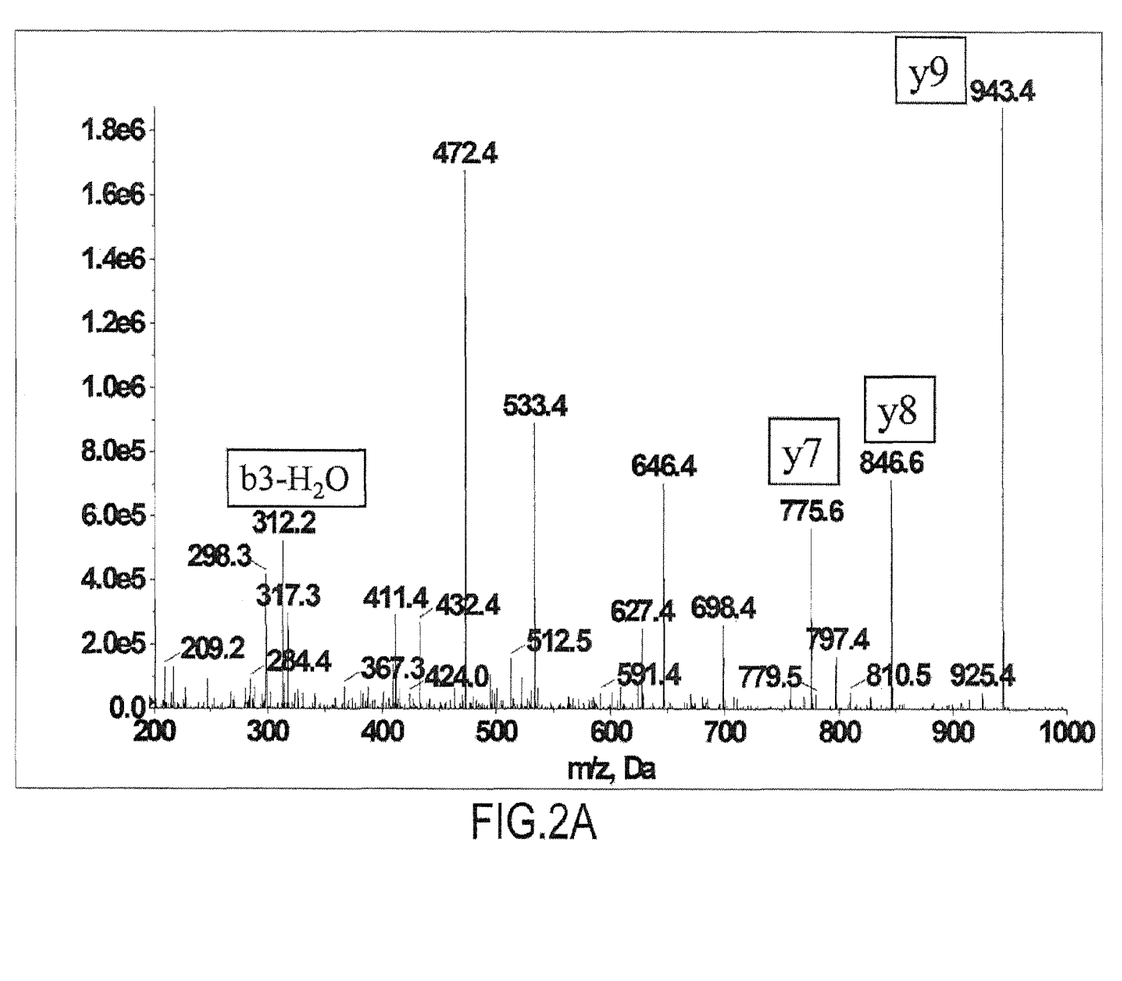
FIG. 2A represents an $MS^2$ spectrum of the 636.8 Th ion at 9.08 minutes for a sample of PSA protein having a concentration of 200 μg/ml in female serum processed in example 2.

In the EPI mode, scanning of all the masses between 200 and 1000 Th makes it possible to obtain a mass spectrum. An example of the spectrum obtained at 9.08 minutes is represented in FIG. 2A for a sample having a concentration of 200 µg/ml of PSA. The scan time is 700 ms at a speed of 1000 Da/s.

Since the chromatographic eluate of the mixture of PSA and serum is injected continuously into the mass spectrometer, it is possible to obtain a signal as a function of time in the form of a chromatogram of first-generation fragment ions. Thus, the first-generation fragment ions y9 (943.5 Th), y8 (846.5 Th), y7 (775.4 Th) and b3 minus one molecule of water (312.2 Th), corresponding to the PSA proteotypic peptide LSEPAELTDAVK (SEQ ID No 6), are eluted between 9 and 9.15 minutes. The sum of the signal obtained for the ions of 943.5, 846.5, 775.4 and 312.2 Th is represented in FIG. 2B for the sample at a concentration of 200 µg/ml of PSA.

Figure 2B:
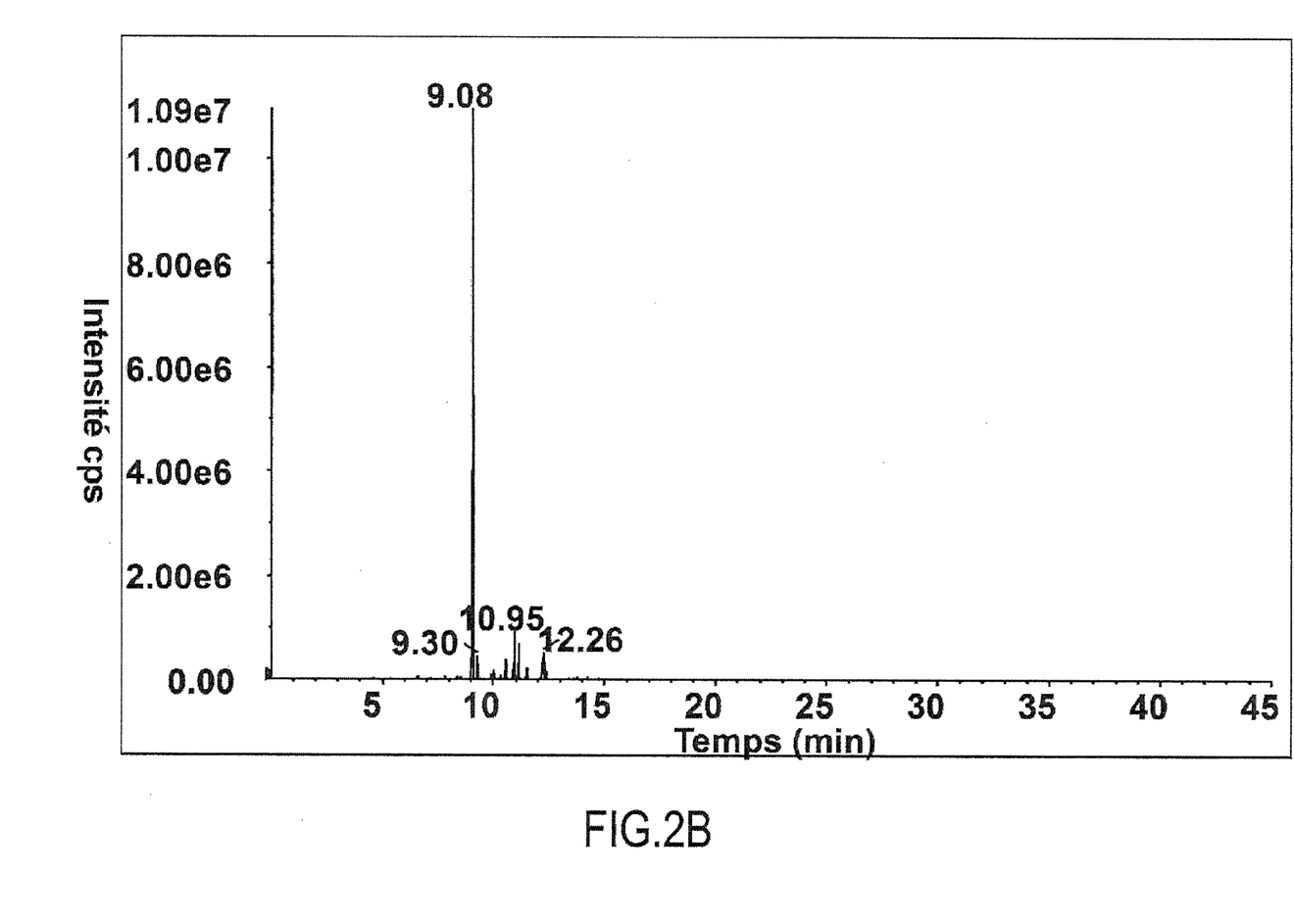
FIG. 2B represents a chromatogram of the sum of the $1^{st}$ generation fragment ions at 9.08 minutes for the sample of PSA having a concentration of 200 μg/ml in female serum processed in example 2.

The Analyst 1.5 software then makes it possible to integrate the area under the peak observed on the chromatogram of FIG. 2B. Thus, the measurement of the signal of the sum of the ions 943.5, 846.5, 775.4 and 312.2 Th made it possible to obtain the results given in TABLE 5 hereinafter:

TABLE 5

| Area under the peaks | PSA concentration (µg/ml) |
|---|---|
| 1.25e+005 | 0 |
| 5.54e+006 | 50 |
| 1.13e+007 | 100 |
| 2.23e+007 | 200 |
| 5.56e+007 | 500 |

Alternatively, the same experiment is carried out by applying the simultaneous expulsion method of the present invention.

To do this, a broadband wave, which comprises the radiofrequencies of the ions to be expelled of m/z 943.5, 846.5, 775.4 and 312.2, is applied. A window of 0.7 mass unit around each m/z value of a first-generation fragment ion to be expelled is used, which means that the radiofrequencies applied form notches of 0.7 mass unit around each m/z value 943.5, 846.5, 775.4 and 312.2 Th. The broadband wave thus applied leads to the ejection of all the first-generation fragment ions in 0.8 ms. The signal obtained is measured. Simultaneous expulsion of all the remaining ions trapped in the trap is then carried out in order to empty it, also in 0.8 ms.

When the signal obtained for each solution having a given concentration of PSA is measured, a single peak is obtained, the area of which is representative of the concentration of target molecule assayed. The areas under each peak corresponding to the signal obtained during the simultaneous ejection of all the first-generation fragment ions for each of the solutions tested are proportional to the PSA concentrations and comparable to those obtained in the EMS mode, except for the point 0 which exhibits a stronger signal. The assay method of the present invention therefore allows a quantitative assay of PSA, via the first-generation fragments of its proteotypic ion LSEPAELTDAVK (SEQ ID No 6), which is as precise as the EPI method, but in a much shorter time.

The use of a shorter analysis time or cycle time would make it possible to successively assay several different products, which is particularly advantageous when a multiplexed assay must be carried out.

Moreover, the background noise observed for the sample at 0 µg/ml of PSA is lower with the method of the invention. The method according to the invention therefore allows a reduction in the background noise compared with the prior art. As it happens, it is well known to those skilled in the art that a decrease in background noise makes it possible to improve measurement sensitivity.

EXAMPLE 3

Measurement of the Concentration of a Protein at Low Concentration in a Complex Mixture with a Mass Spectrometer Having a Triple Quadrupole Q1q2Q3 Configuration, with Two Fragmentation Cycles and the Quadrupole Q3 of which operates in ion-trap mode. MS/MS/MS Analysis A solution of PSA and a female serum, not comprising PSA, are digested according to the protocol of example 2.

After digestion, 100 µl of digested female serum are supplemented with digested PSA so as to obtain solutions with a PSA concentraton of 1000, 500, 100, 50, 10 and 0 ng/ml. Much lower concentrations than in example 2 are used here.

Volumes of 100 µl of the resulting samples are injected onto a chromatography column and then into a mass spectrometer, as processed in the protocol of example 2.

The quadrupole Q1 of the mass spectrometer is used to specifically select the ions of 636.8 Th, with a resolution of 0.7 mass unit. The quadrupole q2 is used to fragment the ions of 636.8 Th into first-generation fragments. The quadrupole Q3 is used to select and fragment the first-generation fragment of 472.3 Th. All of the second-generation fragment ions are then trapped in the trap in Q3.

The analytical results obtained according to the simultaneous expulsion mode proposed by the method of the present invention and the analytical results obtained according to the known MS/MS/MS mode are then compared. This mode is identical to the EPI mode described above in Q1 and q2, but the quadrupole Q3 is used in trap mode for fragmenting the first-generation fragment ion, of 472.3 Th, into a second-generation fragment ion, and then a scan between 500 and 850 Th is carried out in the trap in order to successively expel all the ions.

The other machine parameters used are the same as those of example 1.

Figure 3A:
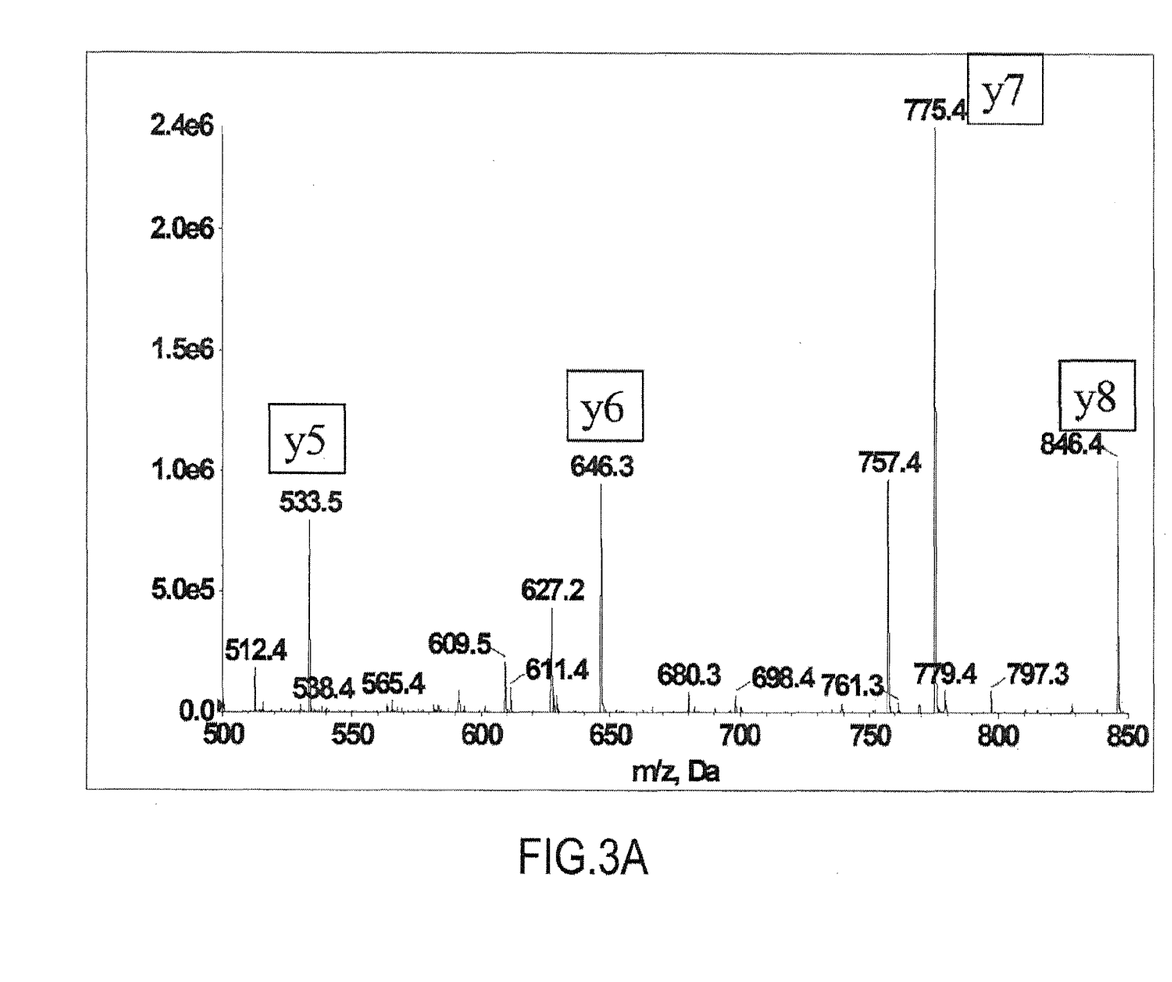
FIG. 3A represents an $MS^3$ spectrum of the $1^{st}$-generation fragment 472.3 Th, resulting from the 636.8 Th precursor ion, between 11.914 and 12.058 minutes, for a sample of PSA having a concentration of 1 μg/ml in female serum processed in example 3.

In the MS/MS/MS mode, the scan of all the masses between 500 and 850 Th makes it possible to obtain the mass spectrum represented in FIG. 3A. The scan time is 350.1 ms at a speed of 1000 Da/s.

The signal induced by the second-generation fragment ions is measured. This signal is proportional to the amount of first-generation fragment ion, which is itself proportional to the amount of proteotypic peptide, which is itself proportional to the amount of PSA protein. The signal is therefore proportional to the amount of PSA protein in the mixture injected and analysed.

Figure 3B:
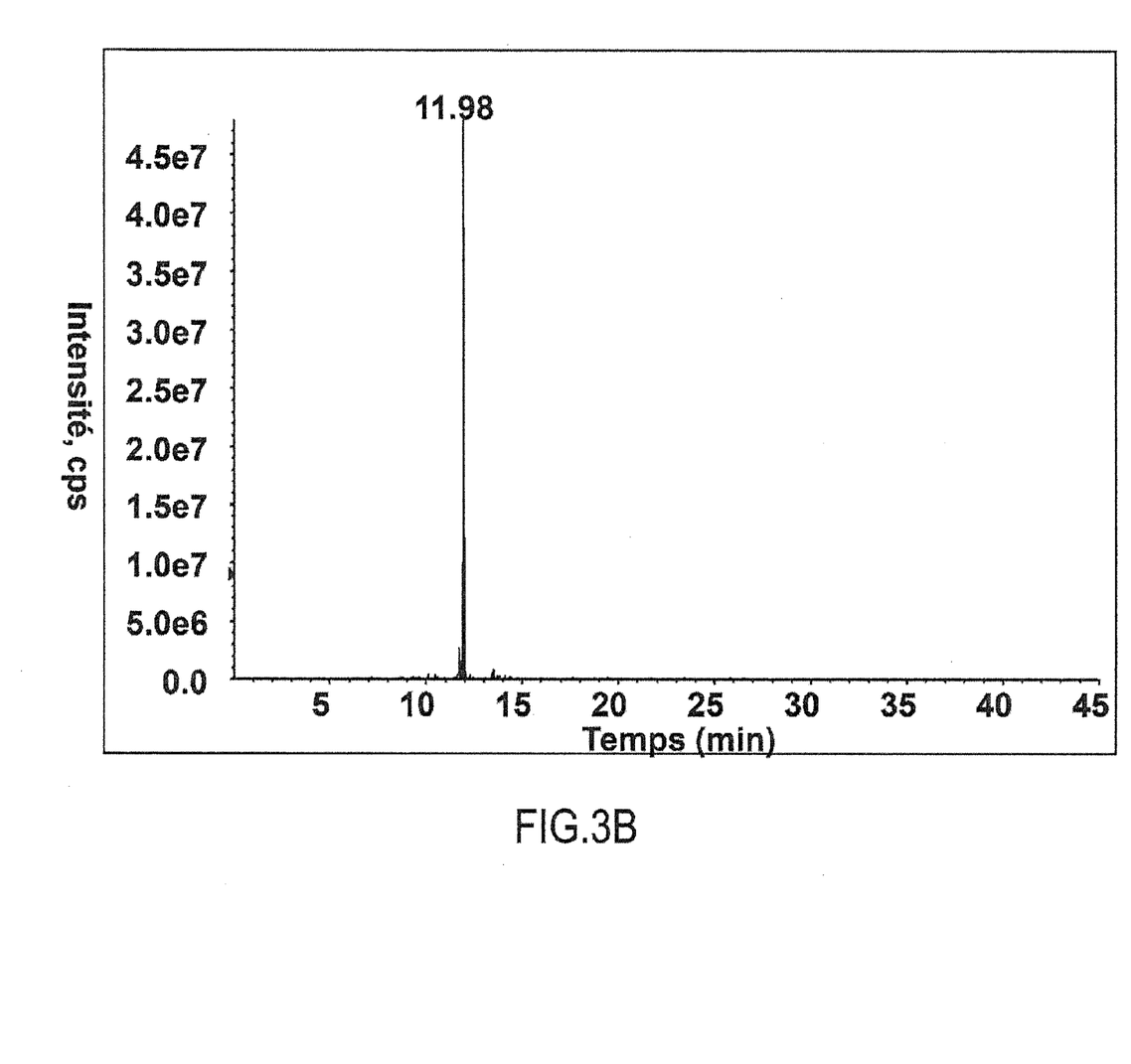
FIG. 3B represents a chromatogram of the sum of the $1^{st}$ generation fragment ions at 11.98 minutes for the sample of PSA having a concentration of 1 μg/ml in female serum processed in example 3.

Since the chromatographic eluate of the mixture of PSA and serum is injected continuously into the mass spectrometer, it is possible to obtain a signal as a function of time in the form of a chromatogram of second-generation fragment ions, as represented in FIG. 3B. Thus, the second-generation fragment ions corresponding to the PSA proteotypic peptide LSEPAELTDAVK (SEQ ID No 6) are eluted between 11.9 and 12.1 minutes.

The Analyst 1.5 software then makes it possible to integrate the area under the peak observed on the chromatogram in FIG. 3B. Thus, the measurement of the signal of the sum of the ions y5 (533.3 Th); y6 (646.4 Th); y7 (775.4 Th) and y8 (846.5 Th), of the peptide LSEPAELTDAVK (SEQ ID No. 6), made it possible to obtain TABLE 6 hereinafter:

TABLE 6

| Area under the peaks | PSA concentration (ng/ml) |
| --- | --- |
| 1.50e+005 | 0 |
| 1.79e+006 | 10 |
| 8.90e+006 | 50 |

TABLE 6-continued

| Area under the peaks | PSA concentration (ng/ml) |
| --- | --- |
| 1.77e+007 | 100 |
| 8.91e+007 | 500 |
| 1.78e+008 | 1000 |

Alternatively, the same experiment is carried out by applying the simultaneous expulsion method of the present invention. As in the previous examples, the simultaneous expulsion in Q3 of the spectrometer is carried out by emission, in said quadrupole Q3, of a broadband wave into which frequency notches corresponding to the resonance frequencies of the second-generation fragment ions y5 (533.3 Th); y6 (646.4 Th); y7 (775.4 Th) and y8 (846.5 Th) are inserted. A window of 0.7 mass unit around each first-generation fragment ion mass is used. The broadband wave thus applied leads to the ejection of all the contaminating ions in 0.8 ms. Simultaneous expulsion of all the remaining ions trapped in the Q3 trap is then carried out in order to empty it, in 0.8 ms, by applying a broadband wave comprising all of the radiofrequencies of the ions between 300 and 700 Th. The signal obtained is measured.

In the analysis mode by expulsion and simultaneous detection, proposed by the invention, the analysis time is 1.6 ms and therefore, as in the previous examples, considerably shorter than that of the MS/MS/MS mode.

When the signal obtained for each solution having a given PSA concentration is measured, a single peak is obtained, the area of which is representative of the concentration of target molecule assayed. The areas under each peak corresponding to the signal obtained during the simultaneous ejection of the second-generation fragment ions for each solution tested are proportional to the PSA concentrations and comparable to those obtained in the EPI mode, except for the point 0 which exhibits a stronger signal.

The principle of the simultaneous ejection of a set of fragment ions specific for the fragmentation of a precursor ion as it has been presented in the previous examples can therefore be extended to the simultaneous ejection of a set of second-generation fragment ions specific for the fragmentation of a first-generation fragment ion.

This application is particularly advantageous when it is necessary to assay with great sensitivity and great specificity, in a multiplexed manner, several molecules in a complex mixture. The present invention is therefore particularly suitable for multiplexed assaying of proteins of clinical interest in the bloodstream.

In the same way as in example 2, for the sample without PSA, a lower background noise is observed for the method with simultaneous expulsion than for the MS/MS/MS method, which means that the method of the present invention is more sensitive.

The invention claimed is:

1. Method for detecting at least one target molecule in a sample by mass spectrometry, in which:
   a) the molecules of the sample are ionized, by means of at least one ionization device, so as to obtain molecular ions,
   b) the following steps (i) and (ii) are carried out n times, n being equal to 0, 1, 2, 3 or 4:
      (i) at least one ion obtained in the preceding step is selected, according to the target molecule, in a mass analyzer, and
      (ii) said at least one ion thus selected is fragmented in a fragmentation cell,
   c) at least two different ions obtained in step a) when n is zero, or in step b) when n is other than zero, are trapped in a mass analyzer, said at least two ions thus trapped being characteristic of the target molecule and having different mass-to-charge ratios m/z, the mass-to-charge ratios m/z being characteristic of the target molecule,
   d) said characteristic ions thus trapped are ejected from the mass analyzer, and
   e) said characteristic ions thus ejected are collected and detected by means of a detection device,
   characterized in that the characteristic ions are ejected simultaneously in step d) and detected simultaneously in step e), wherein the detection device that is used for the simultaneous detection in step e) is used for the collection of all characteristic ions that are simultaneously ejected.

2. Method according to claim 1, characterized in that the mass analyser used in step c) is an ion trap.

3. Method according to claim 2, characterized in that the ion trap is of 3D or linear type.

4. Method according to claim 2, characterized in that the ejection of the characteristic ions in step d) is carried out by making said ions having a mass-to-charge ratio m/z characteristic of the target molecule simultaneously resonate in the ion trap by means of radiofrequency voltages.

5. Method according to claim 1, characterized in that the ions not characteristic of the target molecule are emptied out of the mass analyzer of step c) after the trapping and before the ejection and the detection of the characteristic ions.

6. Method according to claim 1, characterized in that n is equal to 1, 2, 3 or 4 and the mass analyzer used in step b) is an ion trap or a quadrupole analyzer.

7. Method according to claim 6, characterized in that the fragmentation cell is an ion trap.

8. Method according to claim 6, characterized in that step b) and step c) are carried out in the same device, namely in an ion trap.

9. Method according to claim 6, characterized in that n is 1 and the at least two ions trapped in step c) are first-generation fragment ions.

10. Method according to claim 6, characterized in that n is 2 and the at least two ions trapped in step c) are second-generation fragment ions.

11. Method according to claim 1, characterized in that the sample is pretreated for purification purposes.

12. Method according to claim 11, characterized in that the target molecule is a proteotypic peptide of a protein and the sample has been pretreated to generate peptides from a protein of interest.

13. Method according to claim 1, characterized in that, after simultaneous ejection and simultaneous detection, the characteristic ions detected are quantified in order to quantify the target molecule, in particular by establishing a calibration curve or by internal calibration with a molecule similar to the target molecule.

14. Method according to claim 1, wherein the detection of the characteristic ions selected in step e) is carried out by a detector which collects the ions ejected and produces an electrical signal, the strength of which depends on the amount of ions collected, the electrical signal obtained corresponding to all the collected ions which are simultaneously ejected into the detector.

15. Method for detecting at least one target molecule in a sample by mass spectrometry, in which:
   a) the molecules of the sample are ionized, by means of at least one ionization device, so as to obtain molecular ions,
   b) the following steps are carried out:
      (i) at least one ion obtained in the preceding step is selected, according to the target molecule, in a mass analyser, and
      (ii) said at least one ion thus selected is fragmented in a fragmentation cell, so as to give a $1^{st}$-generation fragment ion, then
      (iii) at least one $1^{st}$-generation fragment ion is selected, according to the target molecule, in a mass analyser, and
      (iv) said at least one ion thus selected is fragmented in a fragmentation cell, so as to give at least two second-generation fragment ions,
   c) at least two different second-generation fragment ions obtained in step b) are trapped in a mass analyser, said at least two ions thus trapped being characteristic of the target molecule and having different mass-to-charge ratios m/z, the mass-to-charge ratios m/z being characteristic of the target molecule,
   d) said characteristic ions thus trapped are ejected from the mass analyser, and
   e) said characteristic ions thus ejected are collected and detected by means of a detection device,
   wherein the characteristic ions are ejected simultaneously in step d) and detected simultaneously in step e).

16. Method according to claim 15, wherein the detection device that is used for the simultaneous detection in step e) is used for the collection of all characteristic ions that are simultaneously ejected.

17. Method according to claim 15, wherein ions not characteristic of the target molecule are emptied out of the mass analyzer of step c) after the trapping and before the ejection and the detection of the characteristic ions.

18. Method according to claim 15, characterized in that the mass analyser used in step c) is an ion trap.

19. Method according to claim 18, characterized in that the ion trap is of 3D or linear type.

20. Method according to claim 15, characterized in that the mass analyzer used in step b) is an ion trap or a quadrupole analyser.

21. Method according to claim 15, wherein the detection of the characteristic ions selected in step e) is carried out by a detector which collects the ions ejected and produces an electrical signal, the strength of which depends on the amount of ions collected, the electrical signal obtained corresponding to all the collected ions which are simultaneously ejected into the detector.

\* \* \* \* \*

SEQUENCE LISTING

```
<160> NUMBER OF SEQ ID NOS: 6

<210> SEQ ID NO 1
<211> LENGTH: 141
<212> TYPE: PRT
<213> ORGANISM: artificial sequence
<220> FEATURE:
<223> OTHER INFORMATION: Proteine recombinante TP171 de Treponema
      pallidum

<400> SEQUENCE: 1
```

-continued

```
Met Arg Gly Ser Ala Ser Phe Ser Ser Ile Pro Asn Gly Thr Tyr Arg
1               5                   10                  15

Ala Thr Tyr Gln Asp Phe Asp Glu Asn Gly Trp Lys Asp Phe Leu Glu
            20                  25                  30

Val Thr Phe Asp Gly Gly Lys Met Val Gln Val Val Tyr Asp Tyr Gln
        35                  40                  45

His Lys Glu Gly Arg Phe Lys Ser Gln Asp Ala Asp Tyr His Arg Val
    50                  55                  60

Met Tyr Ala Ser Ser Gly Ile Gly Pro Glu Lys Ala Phe Arg Glu Leu
65                  70                  75                  80

Ala Asp Ala Leu Leu Glu Lys Gly Asn Pro Glu Met Val Asp Val Val
                85                  90                  95

Thr Gly Ala Thr Val Ser Ser Gln Ser Phe Arg Arg Leu Gly Ala Ala
            100                 105                 110

Leu Leu Gln Ser Ala Arg Arg Gly Glu Lys Glu Ala Ile Ile Ser Arg
        115                 120                 125

Gly Ser Ser Lys Tyr Lys Tyr His His His His His
    130                 135                 140
```

```
<210> SEQ ID NO 2
<211> LENGTH: 9
<212> TYPE: PRT
<213> ORGANISM: artificial sequence
<220> FEATURE:
<223> OTHER INFORMATION: Ion proteotypique

<400> SEQUENCE: 2

Glu Leu Ala Asp Ala Leu Leu Glu Lys
1               5

<210> SEQ ID NO 3
<211> LENGTH: 11
<212> TYPE: PRT
<213> ORGANISM: artificial sequence
<220> FEATURE:
<223> OTHER INFORMATION: Ion proteotypique

<400> SEQUENCE: 3

Asp Phe Leu Glu Val Thr Phe Asp Gly Gly Lys
1               5                   10

<210> SEQ ID NO 4
<211> LENGTH: 6
<212> TYPE: PRT
<213> ORGANISM: artificial sequence
<220> FEATURE:
<223> OTHER INFORMATION: Ion proteotypique

<400> SEQUENCE: 4

Glu Ala Ile Ile Ser Arg
1               5

<210> SEQ ID NO 5
<211> LENGTH: 11
<212> TYPE: PRT
<213> ORGANISM: artificial sequence
<220> FEATURE:
<223> OTHER INFORMATION: Ion proteotypique

<400> SEQUENCE: 5

Met Val Gln Val Val Tyr Asp Tyr Gln His Lys
1               5                   10
```

```
<210> SEQ ID NO 6
<211> LENGTH: 12
<212> TYPE: PRT
<213> ORGANISM: artificial sequence
<220> FEATURE:
<223> OTHER INFORMATION: Peptide du PSA

<400> SEQUENCE: 6

Leu Ser Glu Pro Ala Glu Leu Thr Asp Ala Val Lys
1               5                   10
```